US00PP37479P3

(12) United States Plant Patent
Evison

(10) Patent No.: US PP37,479 P3
(45) Date of Patent: Jun. 23, 2026

(54) ***CLEMATIS* PLANT NAMED 'EviGsy156'**

(50) Latin Name: ***Clematis patens* X *Clematis viticella***
Varietal Denomination: EviGsy156

(71) Applicant: Raymond J. Evison Ltd., Vale (GB)

(72) Inventor: Raymond J. Evison, Vale (GB)

(73) Assignee: RAYMOND J. EVISON LTD., Vale (GB)

( * ) Notice: Subject to any disclaimer, the term of this patent is extended or adjusted under 35 U.S.C. 154(b) by 0 days.

(21) Appl. No.: 19/362,179

(22) Filed: Oct. 17, 2025

(65) Prior Publication Data

US 2026/0150768 P1 May 28, 2026

(30) Foreign Application Priority Data

Nov. 27, 2024 (QZ) ..... 20242826

(51) Int. Cl.
*A01H 5/02* (2018.01)
*A01H 6/72* (2018.01)

(52) U.S. Cl.
USPC ..... Plt./228

(58) Field of Classification Search
USPC ..... Plt./228
See application file for complete search history.

(56) References Cited

U.S. PATENT DOCUMENTS

PP28,552 P3 * 10/2017 Olesen ..... Plt./228

* cited by examiner

*Primary Examiner* — Susan Mccormick Ewoldt
(74) *Attorney, Agent, or Firm* — Penny J. Aguirre

(57) ABSTRACT

A new cultivar of *Clematis* plant named 'EviGsy156' that is characterized by its blooms in May and June and reblooms in late August to October, its flowers with tepals that are purple-blue in color with a darker purple-red color through the centers and contrasting red anthers, its compact plant habit; ranging between 90 cm and 1.2 m in height and spread on a current year's growth, its dense foliage, its floriferous blooming habit with repeat blooms, and its high suitability for growing in both gardens and containers.

2 Drawing Sheets

Botanical classification: *Clematis patens* X *Clematis viticella.*

Variety denomination: 'EviGsy156'.

CROSS-REFERENCE TO A RELATED APPLICATION

This application claims priority to European Community Plant Variety Office (CPVO) Plant Breeder's Rights Application No. 2024/2826 filed on Nov. 27, 2024, under 35 U.S.C. 119(f), the entire contents of which is incorporated by reference herein.

BACKGROUND OF THE INVENTION

The present invention relates to a new and distinct cultivar of *Clematis* of hybrid origin (Patens Group) and will be referred to hereafter by its cultivar name 'EviGsy156'. 'EviGsy156' is grown as an herbaceous climbing plant for use in the landscape or as a flowering potted plant for the terrace.

'EviGsy156' derived from an ongoing breeding program by the Inventor in his nursery in Guernsey, The Channel Islands. The goal of the breeding program is to select new cultivars of *Clematis* with compact plant habits with an abundance of flowers that are large in size, present from the base of plant to top of plant with unique flower colors, and strong repeat blooming. 'EviGsy156' was selected as a single unique plant in April of 2020 and arose from a controlled cross made in June of 2015 between unnamed and unpatented seedlings of *Clematis patens* X *Clematis viticella* from the Inventor's breeding program.

Asexual propagation of the new cultivar was first accomplished by stem cuttings under the direction of the Inventor in Guernsey, The Channel Islands in May of 2020. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'EviGsy156' as a unique cultivar of *Clematis*.

1. 'EviGsy156' exhibits blooms in May and June and reblooms in late August to October.
2. 'EviGsy156' exhibits flowers with tepals that are purple-blue in color with a darker purple-red color through the centers and contrasting red anthers.
3. 'EviGsy156' exhibits a compact plant habit, ranging between 90 cm and 1.2 m in height and spread on a current year's growth.
4. 'EviGsy156' exhibits dense foliage.
5. 'EviGsy156' exhibits a floriferous blooming habit with repeat blooms.
6. 'EviGsy156' exhibits high suitability for growing in both gardens and containers.

The female parent of 'EviGsy156' differs from 'EviGsy156' in having flowers with tepals that are violetblue without a darker center and yellow anthers. The male parent of 'EviGsy156' differs from 'EviGsy156' in having flowers with tepals that are pink in color. 'EviGsy156' can be most closely compared to the *Clematis* cultivars 'EVIthree' (U.S. Plant Pat. No. 9,362) and 'Evipo058' (U.S. Plant Pat. No. 28,552). Both 'EVIthree' and 'Evipo058' are similar to 'EviGsy156' in flower coloration. 'EVIthree' differs from 'EviGsy156' in having flowers that are less full and less rounded with narrower tepals, a less compact plant habit, and less repeat flowering. 'Evipo058' differs from 'EviGsy156' in having a dwarf plant habit.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period to the filing date. Disclosures include Raymond Evison *Clematis*, Concept Plants, Donahue's Greenhouse, GrowerTalks, Instagram, Facebook, FloralDaily, Ashwood Nurseries, HelpMeFind, Gardenforum, Pinterest, R.H.S. Digital Collections, Horticulture Week, ipm essen, R.H.S., plantesavenue.fr, Plantipp, Platago, Burford Garden Co., Hortweek, Commercial Horticulture Association, BBC Gardeners' World Live, North Hill Nurseries, Geschlossener Ausstellerbereich, American Floral Endowment, Aktenkraft, angliangardener.co.uk, GOV.UK, Bloemen-en plantennieuws, Woodlands Garden Centre, GTN Xtra, Gabot.de, TASPO.de, Gartenpraxis, DEGA GARTENBAU.

BRIEF DESCRIPTION OF THE DRAWINGS

The accompanying color photographs illustrate the overall appearance and distinct characteristics of the new *Clematis*. The photographs were taken of 2.5-year-old plants of 'EviGsy156' as grown in a 17-cm container in Guernsey, The Channel Islands.

The photograph in FIG. 1 provides view of a plant of 'EviGsy156' in bloom.

Figure 1:
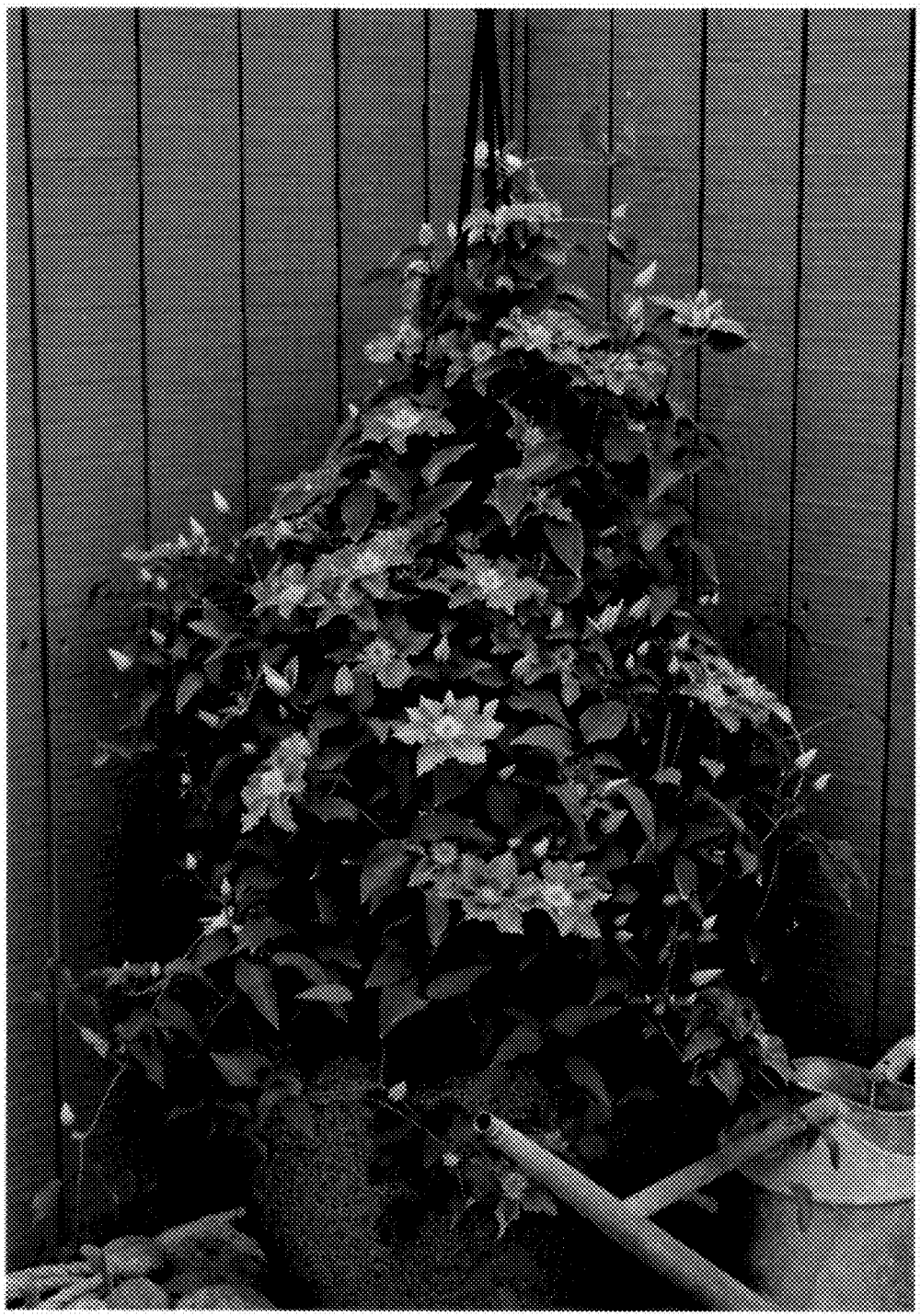
Figure 2:
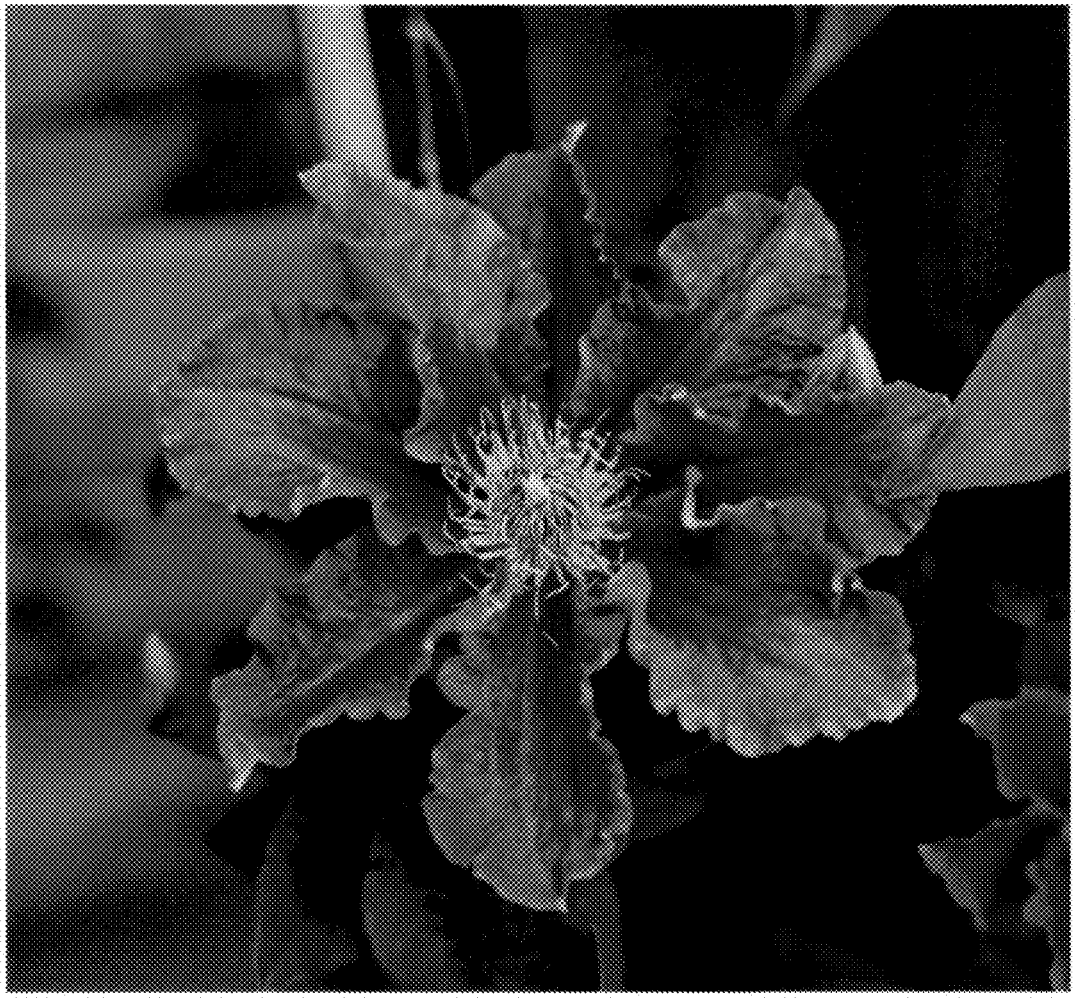

The photograph in FIG. 2 provides a close-up view of a flower of 'EviGsy156'.

The colors in the photographs are as close as possible with the digital photography techniques available, the color values cited in the detailed botanical description accurately describe the colors of the new *Clematis*.

DETAILED BOTANICAL DESCRIPTION

The following is a detailed description of 2.5-year-old plants of 'EviGsy156' as grown in 17-cm containers in Guernsey, The Channel Islands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—Blooms in May and June and reblooms in late August to October in Guernsey, The Channel Islands.

*Plant type*.—Herbaceous woody vine, large flowering *Clematis* that blooms on both old and new wood.

*Plant habit*.—Climber, stems emerge from base, compact.

*Height and spread*.—61 cm in height, 27 cm in width as a 2.5-year-old plant grown in a container, a season's growth reaches 90 to 120 cm in height and spread when grown in the landscape.

*Cold hardiness*.—At least to U.S.D.A. Zone 5.

*Diseases and pests*.—No susceptibility or resistance to pests or diseases has been observed.

*Root description*.—Fleshy.

*Propagation*.—Softwood cuttings from vegetative shoots.

*Time required for root initiation*.—Root initiation takes 3 months, 3 to 4 weeks for roots to appear, another 4 to 6 weeks to produce a fully rooted plug ready for potting, 3 to 6 months for root development from plug to P7 container and 30 weeks for mature plant in a P12 container.

*Growth rate*.—Moderate.

Stem description:

*Shape*.—Round.

*Stem color*.—Young; 144B to 144C, mature; 183A, older stems; 200B to 200C.

*Stem size*.—Length from base to flowering portion of the stem; 36 cm in length, 2 mm in diameter.

*Stem surface*.—Sparsely pubescent.

*Stem strength*.—Strong.

*Internode length*.—Average of 9 cm.

*Branching*.—Basal branching, average of 3 main branches.

Foliage description:

*Leaf arrangement*.—Opposite, ternate.

*Leaf division*.—Compound.

*Leaf attachment*.—Petiolate.

*Leaf quantity*.—26 per branch, 3 leaflets per leaf.

*Leaf size*.—Average of 10 cm in length and 8 cm in width.

*Leaflet shape*.—Ovate.

*Leaflet base*.—Rounded.

*Leaflet apex*.—Acute.

*Leaflet fragrance*.—None.

*Leaflet venation*.—Palmate, color; young upper 144C, lower surface 145A, mature upper 144B, mature lower 144A.

*Leaflet margins*.—Entire.

*Leaflet attachment*.—Petiolule.

*Leaflet surface*.—Upper surface glabrous, lower surface matte.

*Leaflet size*.—Average of 5 cm in length and 3.2 cm in width.

*Leaflet color*.—Young upper surface; 144A, young lower surface 146B, mature upper surface 137A, mature lower surface 147B.

*Petioles*.—Up to 5 cm in length, 1 mm in width, 144B to 144C, flushed with 183B, sparsely pubescent surface.

*Petiolules*.—Up to 4.5 cm in length, 1 mm in diameter, 144B to 144C, flushed with 183B, sparsely pubescent surface.

Inflorescence description:

*Inflorescence type*.—Solitary.

*Inflorescence arrangement*.—Terminal and axillary on new growth.

*Pedicel*.—5 cm in length, 2 mm in diameter, 144B in color, glabrous surface, moderate strength.

*Bud description*.—Ovoid in shape, 3.2 cm in length, 1.3 cm in width, 145C to 145D in color, pubescent surface.

*Flower fragrance*.—No.

*Lastingness of flowers*.—Individual flowers last about 10 days, self-cleaning.

*Flower quantity*.—2 open flowers, 14 buds.

*Flower type*.—Single, rotate, spreading, star-shaped.

*Flower aspect*.—Outward, rotate.

*Flower size*.—9 cm in diameter, 1.5 cm in depth.

*Tepal number*.—6.

*Tepal shape*.—Broadly elliptic.

*Tepal apex*.—Acuminate.

*Tepal base*.—Acute.

*Tepal margins*.—Entire, very light undulations.

*Tepal surface*.—Both surfaces glabrous, satiny, matte.

*Tepal color*.—When opening upper surface; N88A and N89A, center 61A, when opening lower surface; N88A to N88C, center 145D and NN155D, when fully open upper surface; N88A, center 80A, when fully open lower surface N88A, N88C, and NN155D.

*Tepal size*.—Average of 4 cm in length and 2.5 cm in width.

*Receptacle*.—3 mm in depth, 5 mm in width, pubescent surface, round in shape, 144B in color.

Reproductive organs:

*Gynoecium*.—Pistils; 70 to 80, style; 1.1 cm in length, 1 mm in diameter, color; 157D, stigma; slightly superior relative to the length of the filaments and height of the anthers, very small, ovary; 145B and 144B.

*Androecium*.—Stamens; 100, filaments; 1.2 cm in length, glabrous surface, color; NN155A and 157A, base N88C, anthers; 5 mm in length, elongated in shape, 183C in color, glabrous, pollen was not observed.

*Seed*.—Seed head; an average of 2.5 cm in length, 3.6 cm in width, shiny hairs, style; plumose at base, color; 144A to 144B and 165A to 165B, seed development was not observed.

It is claimed:

1. A new and distinct cultivar of *Clematis* plant named 'EviGsy156' as herein illustrated and described.

* * * * *